United States Patent [19]
Yamamoto

[11] Patent Number: 5,857,657
[45] Date of Patent: Jan. 12, 1999

[54] STAND FOR MEDICAL INSTRUMENTS

[75] Inventor: Tetsuya Yamamoto, Osaka, Japan

[73] Assignee: Sugan Co., Ltd., Osaka, Japan

[21] Appl. No.: 959,273

[22] Filed: Oct. 28, 1997

[30] Foreign Application Priority Data

Mar. 17, 1997 [JP] Japan ................................ 9-063396

[51] Int. Cl.$^6$ ................................................ F16M 11/00
[52] U.S. Cl. ................................ 248/406.1; 248/631
[58] Field of Search .................................. 248/158, 132, 248/161, 406.1, 418, 157, 125.2, 592, 600, 631

[56] References Cited

U.S. PATENT DOCUMENTS

| | | | |
|---|---|---|---|
| 5,131,615 | 7/1992 | Hosan et al. | 248/161 |
| 5,284,312 | 2/1994 | Dony | 248/161 |
| 5,443,573 | 8/1995 | Thiele et al. | 248/161 X |
| 5,702,083 | 12/1997 | Lai | 248/161 X |

*Primary Examiner*—Ramon O. Ramirez
*Attorney, Agent, or Firm*—McDermott, Will & Emery

[57] ABSTRACT

In a stand for medical instruments according to the present invention, a first coefficient of friction adapted between an outer circumferential surface of a sliding column and an inner circumferential surface of a bush is adapted to be smaller than a second coefficient of friction caused between an outer circumferential surface of the bush and an inner circumferential surface of a main pipe. This allows a stand for medical instruments which improves operationality.

1 Claim, 4 Drawing Sheets

STAND FOR MEDICAL INSTRUMENTS

BACKGROUND OF THE INVENTION

1. Field of the Invention

The present invention relates to a stand for medical instruments, and particular to a stand for medical instruments for improving the operationality of medical instruments.

2. Description of the Background Art

In recent years, various methods have been developed for testing functions of human body. One of them is X-ray diagnosis on circulatory system for diagnosing the function of the circulatory system of human body. In the X-ray diagnosis on circulatory system, a contrast medium is injected into the body of a patient. In order to inject the contrast medium into the body of a patient, a medical injector head is used. Furthermore, a stand for medical instruments is used to support the medical injector head at the height and position appropriate for the patient.

Referring to FIG. 5, a mechanism of a stand 1B for medical instruments for supporting a conventional medical injector head 100 will now be briefly described. A syringe 101 inside which a contrast medium is sealed is attached to medical injector head 100. The contrast medium sealed inside syringe 101 is injected into a patient through the insertion and ejection of a plunger (not shown) provided in medical injector head 100. A supporting pipe 102 is attached to medical injector head 100.

Stand 1B for medical instruments has a base provided with a plurality of rollers for readily transporting medical injector head 100 to a predetermined position. Attached to base 13 is an upwardly extending, main pipe 8. A gas spring 9 is mounted inside main pipe 8.

Gas spring 9 has an internal space defined by a cylinder and a piston and injected with gas. When a button provided at an end of an externally projecting piston linkage rod, which is linked to the piston, is pressed, the lock mechanism for the piston linkage rod is unlocked and the pressure of the gas causes the piston linkage rod to be pushed out upwards. When the pressed button is released, the piston linkage rod is fixed. The button is pressed and released by an arm 3 provided at the upper end of gas spring 9. Arm 3 is a attached to a head 1 provided at the upper end of gas spring 9.

A head 1 is provided with a handle 2 for readily gripping arm 3. Supporting pipe 102 attached to medical injector head 100 is held at the upper end of head 1.

Thus, stand 1B for medical instruments is structured such that when arm 3 is held and moved, the button provided at gas spring 9 is pressed, the lock mechanism is unlocked and gas spring 9 is slid to any position so as to adjust the level of medical injector head 100 with respect to a patient.

In the above structure, however, when the lock mechanism for gas spring 9 is unlocked, stand 1B can be vertically moved with relatively reduced force so that medical injector head 100 is vertically moved smoothly. Thus, pivotal movement of medical injector head 100 around the axis of gas spring 9 is readily caused.

Thus, when somebody comes in contact with medical injector head 100, for example, during operation of medical injector head 100, the orientation of medical injector head 100 is readily changed, which is often inconvenient in operating medical injector head 100.

SUMMARY OF THE INVENTION

The present invention therefore contemplates a stand for medical instruments that readily moves in the direction of the axis of the gas spring but does not pivot around the axis of the gas spring unless relatively increased force is exerted thereon.

In one aspect of the present invention, a stand for medical instruments includes a gas spring having an internal space defined by a cylinder and a piston and injected with gas. When a button provided at an end of a piston linkage rod externally projecting and linked to the piston is pressed, the lock mechanism for the piston linkage rod is unlocked and the pressure of the gas causes the piston linkage rod to be pushed out. When the pressed button is released, the piston linkage rod is fixed. The stand for medical instruments also includes a sliding column covering the gas spring and coupled with the piston linkage rod such that it is associated with the movement of the piston linkage rod, and a main pipe covering the sliding column and having at its top end an opening through which an end of the sliding column can protrude. The coefficient of friction between the sliding column and the main pipe is adapted to be larger in the pivotal movement of the sliding column around its axis than in the movement of the sliding column in its axial direction.

A stand for medical instruments in another aspect of the present invention includes a gas spring having an internal space defined by a cylinder and a piston and injected with gas. When a button provided at an end of a piston linkage rod externally projecting and linked to the piston is pressed, the lock mechanism for the piston linkage rod is unlocked and the pressure of the gas causes the piston linkage rod to be pushed out. When the pressed button is released, the piston linkage rod is fixed. The stand for medical instruments also includes a base member fixing and supporting the lower end of the gas spring, a sliding column covering the gas spring and coupled with the piston linkage rod such that it is associated with the movement of the piston linkage rod, a bush mounted on an outer circumferential surface of the sliding column such that the bush can slide only in the axial direction of the sliding column, and a main pipe having its lower end fixed to the base member, having at its upper end an opening through which the upper end of the sliding column can project and covering the sliding column such that an inner circumferential surface of the main pipe is brought into contact with an outer circumferential surface of the bush. A first coefficient of friction between the outer circumferential surface of the sliding column and the inner circumferential surface of the bush is adapted to be smaller than a second coefficient of friction between the outer circumferential surface of the bush and the inner circumferential surface of the main pipe.

The coefficient of friction caused between the sliding column and the main pipe is larger in the pivotal movement of the sliding column about the axis of the gas spring than in the movement of the sliding column in the axial direction of the gas spring. Thus, the sliding column can readily slide in moving in the axial direction of the gas spring, while the sliding column does not pivot about the axis the gas spring without exertion of a force larger than that which causes the sliding column to move in the axial direction of the gas spring.

Consequently, when a person comes into contact, for example, with a medical injector head or the like mounted to the upper end of the stand for medical instruments, the orientation of the medical injector head is not readily changed, the operationality of the medical injector head is improved, and a stand for medical instruments which is readily handled by an operator of the medical injector head can be provided.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

A stand for medical instruments according to the present invention will now be described with reference to the figures.

Figure 1:
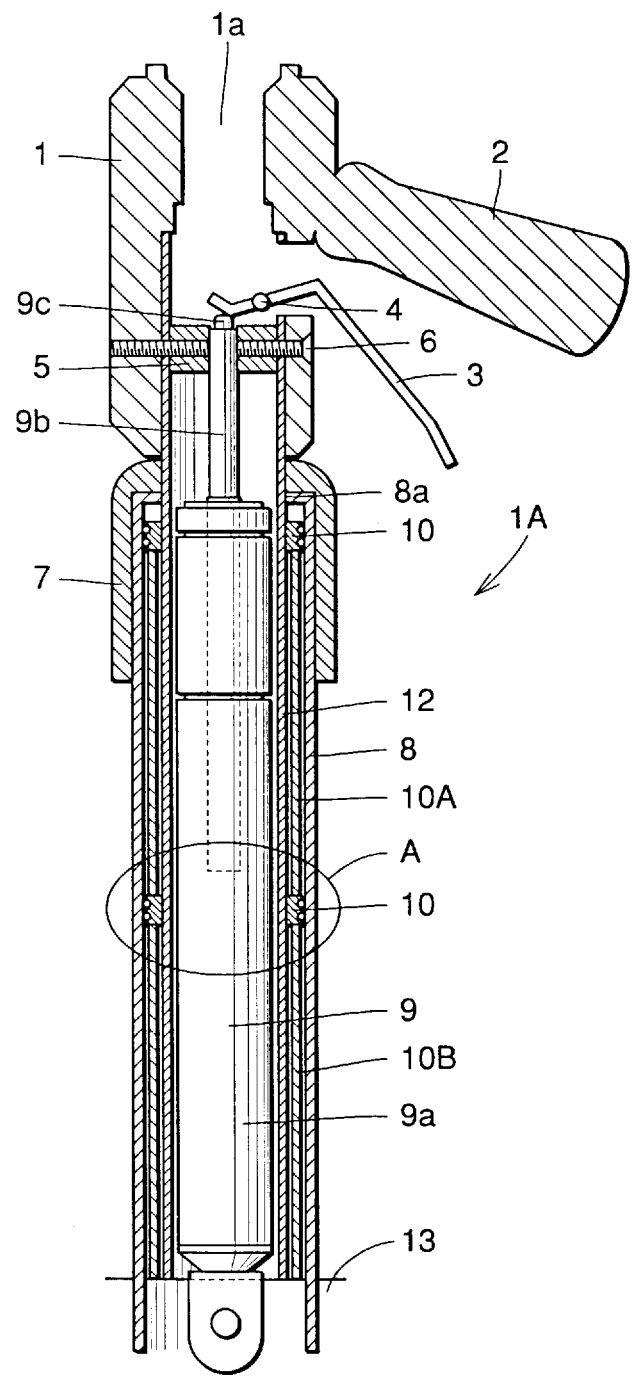
FIG. 1 is a vertical cross sectional view of a stand for medical instruments according to the present invention.

Referring first to FIG. 1, a structure of a stand 1A for medical instruments according to the present embodiment will now be described. Stand 1A for medical instruments includes a gas spring 9. Gas spring 9, the internal structure of which is not detailed in the figure, has an internal space defined by a cylinder and a piston and injected with gas. When a button 9c provided at the upper end of a piston linkage rod 9b externally projecting and linked to the piston is pressed, an internally provided, lock mechanism for piston linkage rod 9b is unlocked and the pressure of the gas inside the cylinder causes piston linkage rod 9b to be pushed out to the outside. When the pressed button 9c is released, the internal lock mechanism fixes piston linkage rod 9b.

Figure 5:
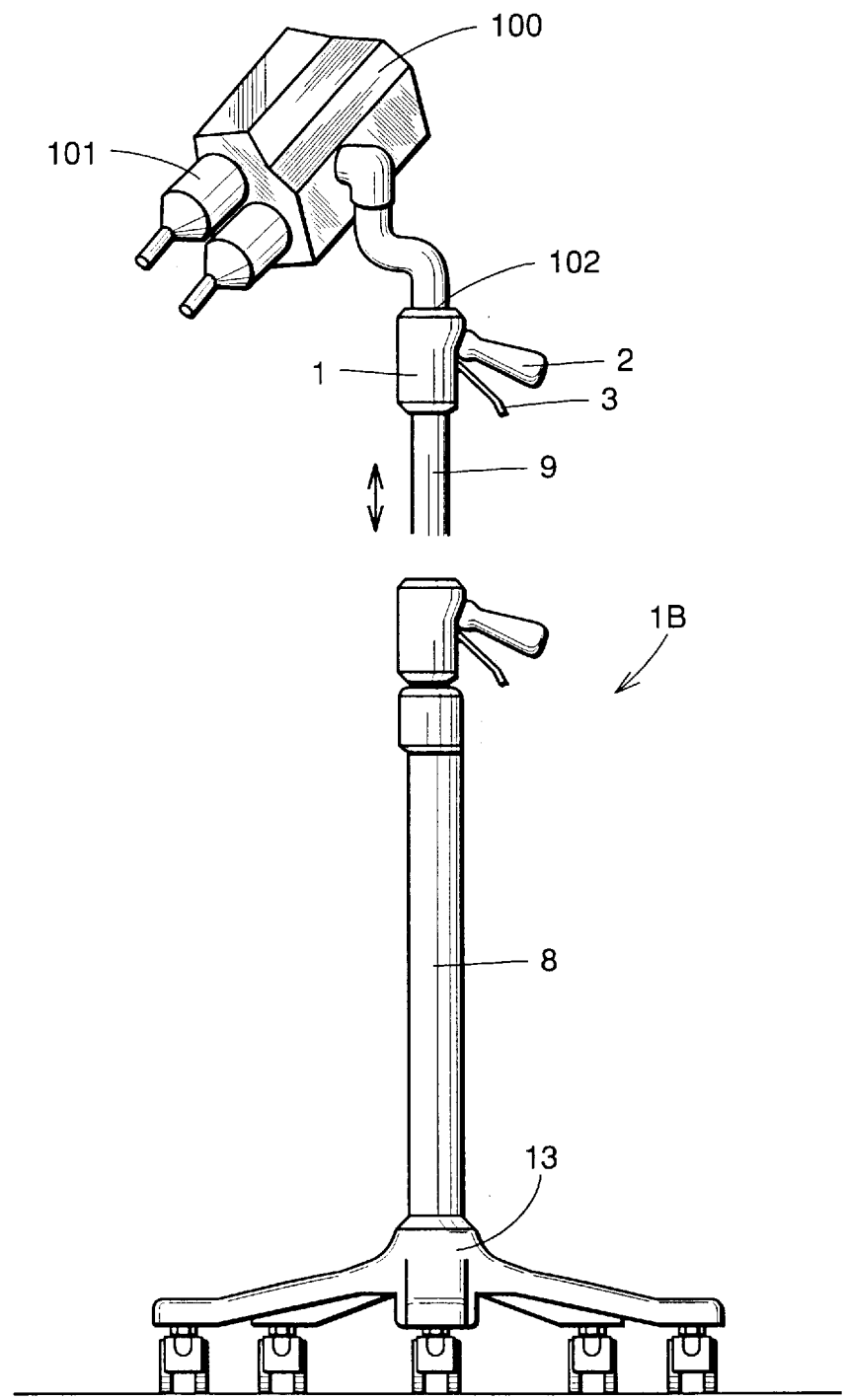
FIG. 5 shows an operation of a stand for medical instruments according to a prior art.

The lower end of the body 9a of gas spring 9 thus structured is fixed to a base 13 which has a similar structure to the that described in connection with the prior art shown in FIG. 5.

Gas spring 9 is covered with a sliding cylindrical column 12 which is coaxially provided with respect to the axis of gas spring 9. Sliding column 12 is fixed to piston linkage rod 9b by a screw 6 with a boss 5 interposed therebetween so that it is associated with the movement of piston linkage rod 9b.

Two bushes 10 are provided on the outer circumferential surface of sliding column 12 such that bushes 10 can slide only in the axial direction of sliding column 12. The structure of bush 10 will be described later. More than two bushes 10 may be provided. In FIG. 1, bushes 10 are positioned by means of supporting pipes 10A and 10B.

Furthermore, a main pipe 8 is provided to cover sliding column 12. The lower end of main pipe 8 is fixed to base 13, and the upper end of main pipe 8 is provided with opening 8a through which the upper end of sliding column 12 can project. An inner circumferential surface of main pipe 8 is in contact with the aforementioned outer circumferential surface of bush 10. In the present embodiment, an upper portion of main pipe 8 is covered with a pipe cover 7.

Figure 2:
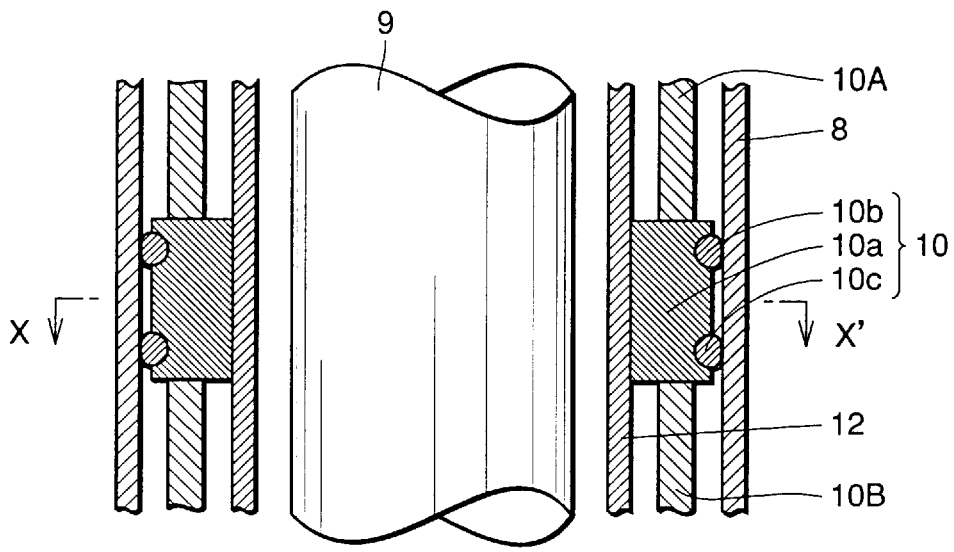
FIG. 2 is a partial cross sectional view of the portion surrounded by circle A shown in FIG. 1.
Figure 3:
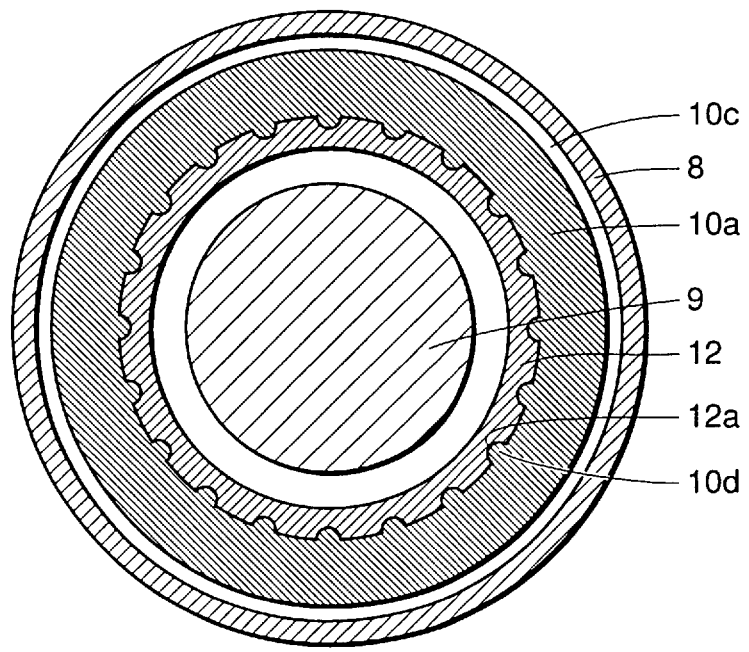
FIG. 3 is a cross sectional view taken along line X–X' shown in FIG. 2, when seen in the direction of the arrow.

The detailed structure of bush 10 will now be described with reference to FIGS. 2 and 3. FIG. 2 is a partially enlarged view of the portion surrounded by circle A shown in FIGS. 1, and FIG. 3 is a cross sectional view taken along line X–X' shown in FIG. 2, when in seen in the direction of the arrows.

Referring to the both figures, the outer surface of sliding column 12 is provided with a plurality of concave grooves 12a in the axial direction of sliding column 12. The inner surface of a body 10a of bush 10 is provided with a convex portion 10d which engages concave groove 12a provided on sliding column 12.

When concave groove 12a engages convex portion 10d, bush body 10a can slide on sliding column 12 only in the axial direction of gas spring 9. Bush 10 is preferably made of teflon so that a possible smallest value of the coefficient of friction is obtained and thus sliding column 12 smoothly slides.

The outer circumferential surface of bush body 10a is provided with an annular groove 10c. A ring member 10b of rubber or the like is pressed into the gap between annual groove 10c and an inner circumferential surface of main pipe 8. Thus, main pipe 8 can pivot about the axis of gas spring 9. However, since ring member 10b is pressed into the gap, the coefficient of friction between ring member 10b and the inner circumferential surface of main pipe 8 is larger than the aforementioned coefficient of friction between sliding column 12 and bush 10a and thus the rotational resistance of sliding column 12 with respect to main pipe 8 around the axis of gas spring 9 is increased. It is not necessary to provide ring members 10b, one for each of annular grooves 10c, and the number of ring members 10b may be smaller than that of annular grooves 10c. The rotational resistance of sliding column 12 with respect to main pipe 8 around the axis of gas spring 9 can be controlled depending on the number of ring members 10b.

Referring again to FIG. 1, a head 1 provided with an insertion hole 1a for mounting a medical instrument is fixed on an upper portion of sliding column 12 by the aforementioned screw 6. Head 1 is provided with an arm 3 with a fulcrum 4, for pressing button 9c provided at gas spring 9, and head 1 is also provided with a handle 2 so that arm 3 readily pivots about fulcrum 4.

Figure 4:
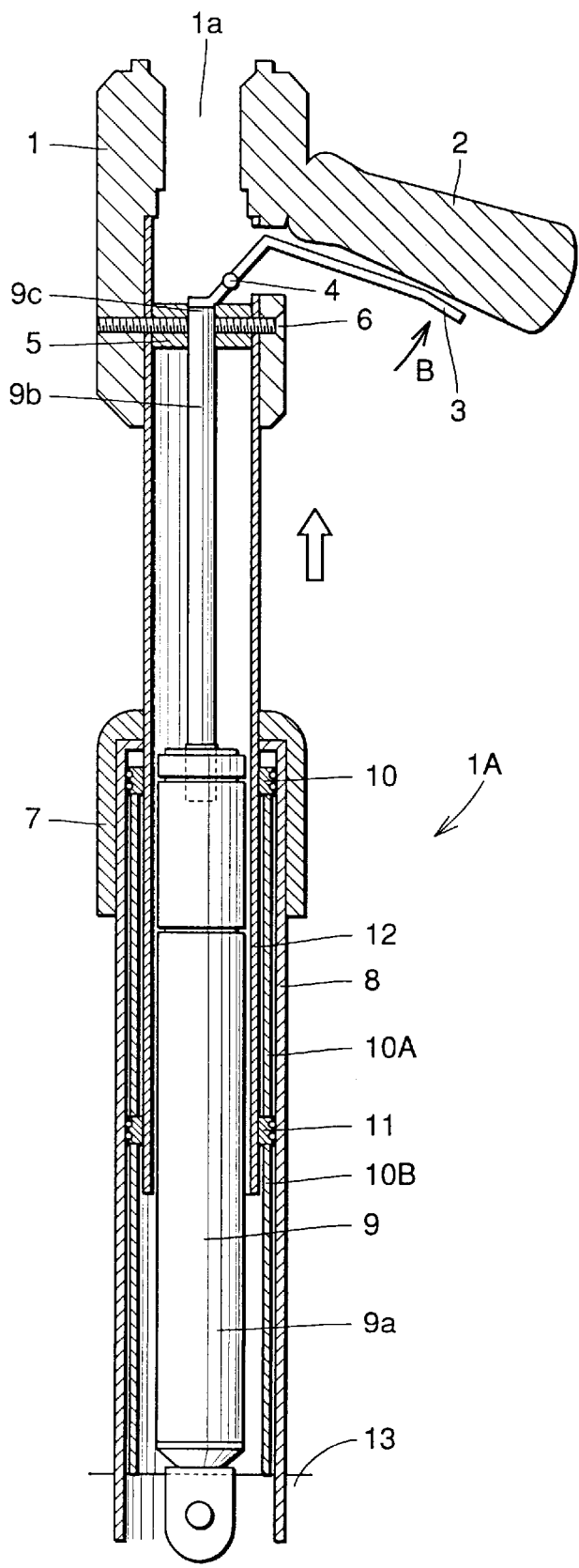
FIG. 4 shows an operation of a stand for medical instruments according to the present invention.

In the stand for medical instruments thus structured, when arm 3 is moved while holding handle 2, button 9c is pressed, the lock mechanism for piston linkage rod 9b is unlocked and sliding column 12 can be readily moved upwards, as shown in FIG. 4. Meanwhile, sliding column 12 pivots with respect to main pipe 8 with ring member 10b interposed therebetween, as described above, the coefficient of friction is thus increased and thus the pivotal movement of sliding column 12 with respect to main pipe 8 requires a force larger than the upward movement of sliding column 12 with respect to main pipe 8.

Thus, when a person comes into contact with the stand thus structured for medical instruments which is mounted, for example, with a medical injector head or the like, the orientation of the medical injector head is not readily changed, the operationality of the medical injector head is improved, and thus a stand for medical instruments which is readily handled by an operator of the medical injector head can be provided.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A stand for medical instruments, using a gas spring having an internal space defined by a cylinder and a piston and injected with gas, said piston being linked to a piston linkage rod projecting externally and provided with a button at an upper end, said piston linkage rod being pushed out by a pressure of said gas when said button is pressed to unlock a lock mechanism for said piston linkage rod, said piston linkage rod being fixed when the pressed said button released, comprising:

a base member fixing and supporting a lower end of said gas spring;

a sliding column covering said gas spring and coupled with said piston linkage rod such that it is associated with a movement of said piston linkage rod;

a bush mounted on an outer circumferential surface of said sliding column such that said bush can slide only in an axial direction of said gas spring; and a main pipe fixed to said base member at a lower end, having at an upper end an opening through which an upper end of said sliding column can protrude, and covering said sliding column such that an inner circumferential surface thereof is in contact with an outer circumferential surface of said bush; wherein a first coefficient of friction caused between the outer circumferential surface of said sliding column and an inner circumferential surface of said bush is adapted to be smaller than a second coefficient of friction caused between the outer circumferential surface of said bush and the inner circumferential surface of said main pipe.

* * * * *